US011435494B1

(12) United States Patent
Wang et al.

(10) Patent No.: US 11,435,494 B1
(45) Date of Patent: Sep. 6, 2022

(54) METHOD FOR PREDICTING OIL ACCUMULATION DEPTH LIMIT OF DEEP AND ULTRA-DEEP MARINE CARBONATE RESERVOIRS

(71) Applicant: INSTITUTE OF GEOLOGY AND GEOPHYSICS, CHINESE ACADEMY OF SCIENCES, Beijing (CN)

(72) Inventors: Wenyang Wang, Beijing (CN); Rixiang Zhu, Beijing (CN); Xiongqi Pang, Beijing (CN); Zhangxing Chen, Beijing (CN); Yaping Wang, Beijing (CN); Tao Hu, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/691,126

(22) Filed: Mar. 10, 2022

(30) Foreign Application Priority Data

Oct. 26, 2021 (CN) .......................... 202111248285.7

(51) Int. Cl.
 *G01V 1/50* (2006.01)
 *G01N 33/28* (2006.01)
(52) U.S. Cl.
 CPC .......... *G01V 1/50* (2013.01); *G01N 33/2823* (2013.01); *G01V 2210/6244* (2013.01)
(58) Field of Classification Search
 CPC . G01V 1/50; G01V 2210/624; G01N 33/2823
 See application file for complete search history.

(56) References Cited

U.S. PATENT DOCUMENTS 9,470,665 B2 * 10/2016 Eisenhauer ............ G01N 30/06
10,161,891 B1 * 12/2018 Tian ........................ G01N 33/24

FOREIGN PATENT DOCUMENTS

CN 103926632 A 7/2014
CN 104453881 A 3/2015
(Continued)

OTHER PUBLICATIONS

Xiongqi Pang, et al, "A unified model for the formation and distribution of both conventional and unconventional hydrocarbon reservoirs", vol. 12, Issue 2, pp. 695-711, (Year: 2020).*

(Continued)

*Primary Examiner* — Ian J Lobo
(74) *Attorney, Agent, or Firm* — Bayramoglu Law Offices LLC

(57) ABSTRACT

A method, system and device for predicting an oil accumulation depth limit of deep and ultra-deep marine carbonate reservoirs is provided. The method includes: obtaining geological factors acting on a porosity of a deep/ultra-deep marine carbonate reservoir, standardizing absolute values of the geological factors; calculating a porosity of the deep/ultra-deep marine carbonate reservoir; acquiring ratios of oil, water and dry layers in each M % porosity interval, and acquiring a relationship between a dry layer ratio and the porosity of the deep/ultra-deep marine carbonate reservoir; recursively obtaining a relationship between the dry layer ratio and the burial depth and determining the oil accumulation depth limit of the deep/ultra-deep marine carbonate reservoir. The method, system and device solves the problem that the prior art cannot by predicting the oil accumulation depth limit directly through the relationship between the dry layer ratio and the depth.

13 Claims, 6 Drawing Sheets

(56) References Cited

FOREIGN PATENT DOCUMENTS

| CN | 104751002 A | 7/2015 |
|----|-------------|--------|
| CN | 104806232 A | 7/2015 |
| CN | 110244357 A | 9/2019 |

OTHER PUBLICATIONS

Hang Jiang, et al., Lower limit of hydrocarbon accumulation in the Kuqa Depression, Tarim Basin, NW China, Geological Journal, 2016.

Yang Gui-Qian, et al., Reservoir characteristics and controlling factors of the Jurassic Badaowan Formation in Zhongguai Uplift, Junggar Basin, Natural Gas Geoscience, 2017, pp. 1689-1698, vol. 28, No. 11.

Wenyang Wang, et al., Improved methods for determining effective sandstone reservoirs and evaluating hydrocarbon enrichment in petroliferous basins, Applied Energy, 2020, pp. 1-13, vol. 261, 11457.

Wang Jiandong, et al., Lower Limits of Physical Properties of Jurassic Tight Sandstone Reservoirs in Block 4 of Central Junggar Basin, Xinjiang Petroleum Geology, 2018, pp. 609-613, vol. 39, No. 5.

Song Mingshui, et al., Lower Limits of Physical Properties of Effective Carboniferous Igneous Reservoir in SU13 Well Block of West Junggar Basin, Journal of Geomechanics, 2019, pp. 1075-1081, vol. 25, No. 6.

* cited by examiner

METHOD FOR PREDICTING OIL ACCUMULATION DEPTH LIMIT OF DEEP AND ULTRA-DEEP MARINE CARBONATE RESERVOIRS

CROSS REFERENCE TO THE RELATED APPLICATIONS

This application is based upon and claims priority to Chinese Patent Application No. 202111248285.7, filed on Oct. 26, 2021, the entire contents of which are incorporated herein by reference.

TECHNICAL FIELD

The present invention belongs to the technical field of oil and gas exploration, and in particular relates to a method, system and device for predicting the oil accumulation depth limit of deep and ultra-deep marine carbonate reservoirs.

BACKGROUND

Marine carbonate rocks are found widely in China, with an area greater than $4.50 \times 10^6$ km². The assessment of the Ministry of Natural Resources (formerly Ministry of Land and Resources) of the People's Republic of China shows that in the field of marine carbonate reservoirs in China, the geological resources of petroleum reach $3.40 \times 10^{10}$ t, and the geological resources of natural gas reach $2.43 \times 10^{13}$ m³. In recent years, oil and gas exploration in the superimposed basins in western China has continued to move to the deep layers of the basins, with the number of deep wells and the drilling depth increasing year by year. The deep oil and gas exploration in the Tarim Basin is at the forefront of the world. In the past 10 years, 1,592 deep oil and gas wells have been drilled in the Tarim Basin, with an average depth of more than 6,043 m accounting for 87% of the total wells, and increasing from an average of 5,231 m in 2006 to 6,665 m in 2017. In 2019, PetroChina completed the drilling of the well Luntan 1 at a depth of 8,882 m in the Tarim Basin, making it now the deepest well in Asia, and discovered the deepest industrial oil reservoir below 8,200 m. Deep and ultra-deep marine carbonate rocks have offered a new field of exploration, and geologists are concerned about the prospect and depth of oil exploration in this field. The oil accumulation depth limit is a depth corresponding to a 100% dry layer ratio. In China, although the drilling depth has exceeded 8,882 m, this is not the oil accumulation depth limit. The study on the oil accumulation depth limit of deep and ultra-deep marine carbonate reservoirs is of great significance for in-depth understanding of the oil exploration prospects in this field and scientific guidance for deep and ultra-deep oil drilling. However, the prior art cannot predict the oil accumulation depth limit directly through the relationship between the dry layer ratio and the depth. Based on this, the present invention proposes a method for predicting the oil accumulation depth limit of deep and ultra-deep marine carbonate reservoirs.

SUMMARY

In order to solve the problem that the prior art cannot predict the oil accumulation depth limit directly through the relationship between the dry layer ratio and the depth, the present invention proposes a method for predicting the oil accumulation depth limit of deep and ultra-deep marine carbonate reservoirs. The method includes the following steps:

S100: obtaining geological factors acting on a porosity of a deep/ultra-deep marine carbonate reservoir and standardizing absolute values of the geological factors; wherein, the geological factors include a geological age, a dynamic deformation, a burial depth, a formation temperature and homogeneity of the deep/ultra-deep marine carbonate reservoir;

S200: calculating modeling coefficients of a mathematical model of sediment compaction and diagenesis in a petroliferous basin, based on influence coefficients corresponding to the geological factors in combination with standardized absolute values of the geological factors, calculating, based on the modeling coefficients, relative compaction and diagenesis of the deep/ultra-deep marine carbonate reservoir by the mathematical model of the sediment compaction and diagenesis in the petroliferous basin, calculating the porosity of the deep/ultra-deep marine carbonate reservoir, and fitting a relationship between the porosity and the burial depth of the deep/ultra-deep marine carbonate reservoir;

S300: analyzing, based on collected formation testing data and logging data, oil, gas and water layers encountered during drilling in a target interval, acquiring ratios of oil, water and dry layers in each M % porosity interval, and acquiring a relationship between a dry layer ratio and the porosity of the deep/ultra-deep marine carbonate reservoir, where the porosity interval is closed first and open last; and S400: recursively obtaining, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth, and determining an oil accumulation depth limit of the deep/ultra-deep marine carbonate reservoir.

In some preferred implementation, the absolute values of the geological factors are standardized as follows:
  geological age of the deep/ultra-deep marine carbonate reservoir, A/Ma: $T_A=0.0125A$;
  dynamic deformation N/tectonostratigraphic unit: $T_N=0.2+1.46 \log N$;
  burial depth of the deep/ultra-deep marine carbonate reservoir, H/km: $T_H=0.1H$;
  formation temperature of the deep/ultra-deep marine carbonate reservoir, t/° C.: $T_t=0.005t$; and
  homogeneity of the deep/ultra-deep marine carbonate reservoir, S: $S=100\% * r_a/r_{max}$, where $r_a$ denotes an average pore throat radius, and $r_{max}$ denotes a maximum connected pore throat radius.

In some preferred implementation, the modeling coefficients of the mathematical model of the sediment compaction and diagenesis in the petroliferous basin are calculated as follows:

$$x_i = \exp(-a_j T)$$

where, $x_i$ denotes the modeling coefficients, $a_j$ denotes the influence coefficients, and T denotes standardized geological factors.

In some preferred implementation, the mathematical model of the sediment compaction and diagenesis in the petroliferous basin is:

$$U_t = U_0 \Pi_{i=1}^n x_i$$

where, $U_t$ denotes current sediment compaction and diagenesis, and $U_0$ denotes initial sediment compaction and diagenesis.

In some preferred implementation, the relative compaction and diagenesis of the deep/ultra-deep marine carbonate reservoir is calculated as follows:

$$Z=U_t/U_0=\Pi_{i=1}^n x_i$$

where, Z denotes the relative compaction and diagenesis of the deep/ultra-deep marine carbonate reservoir.

In some preferred implementation, the porosity of the deep/ultra-deep marine carbonate reservoir is calculated as follows:

$$\phi=\phi_0 Z_1$$

$$Z_1=\Pi_{i=1}^n x_i/[1-\phi_0(1-\Pi_{i=1}^n x_i)]$$

where, $\phi$ denotes a current porosity of the deep/ultra-deep marine carbonate reservoir, $\phi_0$ denotes an initial porosity of the deep/ultra-deep marine carbonate reservoir before compaction and diagenesis, and $Z_1$ denotes a relative change value of the porosity.

A second aspect of the present invention proposes a system for predicting the oil accumulation depth limit of deep and ultra-deep marine carbonate reservoirs, including: a geological factor standardization module, a porosity calculation module, a relationship acquisition module, and a depth limit determination module, where the geological factor standardization module is used for: obtaining geological factors acting on a porosity of a deep/ultra-deep marine carbonate reservoir and standardizing absolute values of the geological factors, where the geological factors include a geological age, a dynamic deformation, a burial depth, a formation temperature and homogeneity of the deep/ultra-deep marine carbonate reservoir;

the porosity calculation module is used for: calculating modeling coefficients of a mathematical model of sediment compaction and diagenesis in a petroliferous basin, based on influence coefficients corresponding to the geological factors in combination with standardized absolute values of the geological factors, calculating, based on the modeling coefficients, relative compaction and diagenesis of the deep/ultra-deep marine carbonate reservoir by the mathematical model of the sediment compaction and diagenesis in the petroliferous basin, calculating the porosity of the deep/ultra-deep marine carbonate reservoir, and fitting a relationship between the porosity and the burial depth of the deep/ultra-deep marine carbonate reservoir;

the relationship acquisition module is used for: analyzing, based on collected formation testing data and logging data, oil, gas and water layers encountered during drilling in a target interval; acquiring ratios of oil, water and dry layers in each M % porosity interval and acquiring a relationship between a dry layer ratio and the porosity of the deep/ultra-deep marine carbonate reservoir, where the porosity interval is closed first and open last; and the depth limit determination module is used for: recursively obtaining, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determining the oil accumulation depth limit of the deep/ultra-deep marine carbonate reservoir.

A third aspect of the present invention provides an electronic device, including:

at least one processor and a memory communicatively connected to the at least one processor, where the memory stores an instruction executable by the processor and the instruction is executed by the processor to implement the above method for predicting the oil accumulation depth limit of deep and ultra-deep marine carbonate reservoirs.

The present invention has the following beneficial effects:

The present invention solves the problem that the prior art cannot predict the oil accumulation depth limit directly through the relationship between the dry layer ratio and the depth.

The present invention finally establishes a method for predicting the oil accumulation depth limit of deep and ultra-deep marine carbonate reservoirs by means of statistical analysis and numerical simulation. The present invention is of great significance for revealing the prospect of deep and ultra-deep marine carbonate reservoir exploration and scientifically guiding deep and ultra-deep oil drilling. The present invention provides theoretical guidance for the evaluation of deep and ultra-deep oil exploration prospects, and provides technical support for guiding deep and ultra-deep oil drilling.

BRIEF DESCRIPTION OF THE DRAWINGS

Other features, objectives and advantages of the present invention will become more apparent upon reading the detailed description of the non-restrictive embodiments made below with reference to the drawings.

DETAILED DESCRIPTION OF THE EMBODIMENTS

In order to make the objectives, technical solutions and advantages of the embodiments of the present invention clearer, the technical solutions in the embodiments of the present invention will be clearly and completely described below in conjunction with the drawings in the embodiments of the present invention. Obviously, the described embodiments are some, rather than all of the embodiments of the present invention. All other embodiments obtained by those of ordinary skill in the art based on the embodiments of the present invention without creative efforts should fall within the protection scope of the present invention.

The present invention will be further described in detail below with reference to the drawings and embodiments. It may be understood that the specific embodiments described herein are merely intended to explain the related invention, rather than to limit the present invention. It should be noted that the embodiments in the present invention and features in the embodiments may be combined with each other if no conflict occurs.

Figure 1:
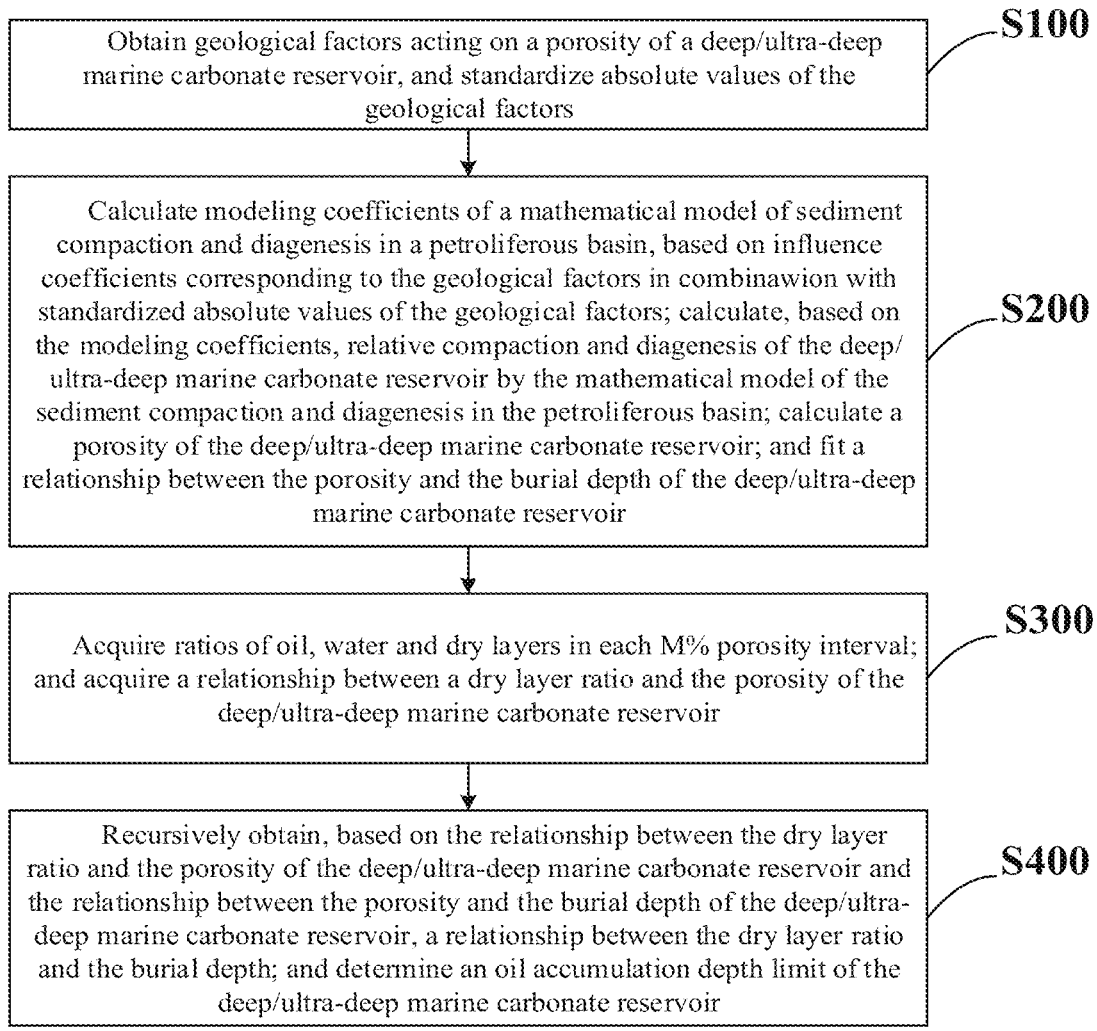
FIG. 1 is a flowchart of a method for predicting the oil accumulation depth limit of deep and ultra-deep marine carbonate reservoirs according to an embodiment of the present invention.

A first embodiment of the present invention provides a method for predicting the oil accumulation depth limit of deep and ultra-deep marine carbonate reservoirs. As shown in FIG. 1, the method includes the following steps:

S100: Obtain geological factors acting on a porosity of a deep/ultra-deep marine carbonate reservoir, and standardize absolute values of the geological factors, where the geological factors include a geological age, a dynamic deformation, a burial depth, a formation temperature and homogeneity of the deep/ultra-deep marine carbonate reservoir.

S200: Calculate modeling coefficients of a mathematical model of sediment compaction and diagenesis in a petroliferous basin, based on influence coefficients corresponding to the geological factors in combination with standardized absolute values of the geological factors, calculate, based on the modeling coefficients, relative compaction and diagenesis of the deep/ultra-deep marine carbonate reservoir by the mathematical model of the sediment compaction and diagenesis in the petroliferous basin, and calculate the porosity of the deep/ultra-deep marine carbonate reservoir; and fit a relationship between the porosity and the burial depth of the deep/ultra-deep marine carbonate reservoir.

S300: Analyze, based on collected formation testing data and logging data, oil, gas and water layers encountered during drilling in a target interval, acquire ratios of oil, water and dry layers in each M % porosity interval, and acquire a relationship between a dry layer ratio and the porosity of the deep/ultra-deep marine carbonate reservoir, where the porosity interval is closed first and open last.

S400: Recursively obtain, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determine an oil accumulation depth limit of the deep/ultra-deep marine carbonate reservoir.

In order to more clearly describe the method for predicting the oil accumulation depth limit of deep and ultra-deep marine carbonate reservoirs, the steps of an embodiment of the method are described in detail below with reference to the drawings.

The present invention adopts the following technical solution: a method for predicting the oil accumulation depth limit of deep and ultra-deep marine carbonate reservoirs. The method includes the following steps: 1) characterize an evolution process of a porosity of a deep or ultra-deep marine carbonate reservoir with a burial depth thereof; 2) determine a relationship between the porosity of the deep or ultra-deep marine carbonate reservoir and a dry layer ratio; and 3) determine a relationship between the dry layer ratio and the burial depth according to the relationship between the porosity and the dry layer ratio and a relationship between the porosity and the burial depth, and determine an oil accumulation depth limit of the deep or ultra-deep marine carbonate reservoir. The technical solution specifically includes:

S100: Obtain geological factors acting on a porosity of a deep/ultra-deep marine carbonate reservoir and standardize absolute values of the geological factors, where the geological factors include a geological age, a dynamic deformation, a burial depth, a formation temperature and homogeneity of the deep/ultra-deep marine carbonate reservoir.

This embodiment applies a mathematical model proposed by Buryakovsky and Dzhevanshir in 1976 for calculating the sediment compaction and diagenesis in the petroliferous basin, which is basically expressed as follows:

$$U_t = U_0 \Pi_{i=1}^n x_i \tag{1}$$

where, $U_t$ denotes current sediment compaction and diagenesis, and $U_0$ denotes initial sediment compaction and diagenesis.

A necessary condition for the mathematical model of the sediment compaction and diagenesis in the petroliferous basin is that each of model coefficients (also called modeling coefficients) $x_i$ is independent, which mainly considers the effects of geological factors on the porosity of the deep/ultra-deep marine carbonate reservoir. The geological factors include a geological age of the deep/ultra-deep marine carbonate reservoir, a dynamic deformation experienced by the deep/ultra-deep marine carbonate reservoir after formation (i.e. number of tectonic cycles), and a burial depth, a formation temperature and homogeneity of the deep/ultra-deep marine carbonate reservoir. For convenience of calculation, the absolute values of the geological factors should be standardized, and standardization formulas of the geological factors were derived (Table 1) through years of research.

TABLE 1

| Geological factor | Standardization formula |
| --- | --- |
| Geological age A/Ma | $T_A = 0.00125A$ |
| Dynamic deformation N/tectonostratigraphic unit | $T_N = 0.2 + 1.46 \log N$ |
| Burial depth H/km | $T_H = 0.1H$ |
| Formation temperature t/° C. | $T_t = 0.005t$ |
| Homogeneity S | $S = 100\% * r_a/r_{max}$ | where, $r_a$ denotes an average pore throat radius, and $r_{max}$ denotes a maximum connected pore throat radius.

S200: Calculate modeling coefficients of a mathematical model of sediment compaction and diagenesis in a petroliferous basin, based on influence coefficients corresponding to the geological factors in combination with standardized absolute values of the geological factors, calculate, based on the modeling coefficients, relative compaction and diagenesis of the deep/ultra-deep marine carbonate reservoir by the mathematical model of the sediment compaction and diagenesis in the petroliferous basin, calculate the porosity of the deep/ultra-deep marine carbonate reservoir, and fit a relationship between the porosity and the burial depth of the deep/ultra-deep marine carbonate reservoir.

The influence factors have different degrees of influence on the porosity of the deep/ultra-deep marine carbonate reservoirs. Through a large number of experimental studies, it is determined that the influence coefficients include three grades of strong, medium and weak, as shown in Table 2.

TABLE 2

| Degree of influence | Strong | Medium | Weak |
|---|---|---|---|
| Influence coefficient | 0.968 | 0.714 | 0.511 |
| Geological factor | Geological age, dynamic deformation, burial depth, formation temperature | Homogeneity | — |

In this embodiment, modeling coefficients of the mathematical model of the sediment compaction and diagenesis in the petroliferous basin are calculated according to Eq. (2) based on the influence coefficients corresponding to the geological factors in combination with the standardized absolute values of the geological factors.

$$x_i = \exp(-a_j T) \quad (2)$$

where, $x_i$ denotes the modeling coefficients, $a_j$ denotes the influence coefficients (as shown in Table 2), and T denotes standardized geological factors (as shown in Table 1).

Based on the modeling coefficients, relative compaction and diagenesis of the deep/ultra-deep marine carbonate reservoir, that is, a relative change of a rock in the deep/ultra-deep marine carbonate reservoir, is calculated according to Eq. (3) by the mathematical model of the sediment compaction and diagenesis in the petroliferous basin.

$$Z = U_t/U_0 = \Pi_{i=1}^n x_i \quad (3)$$

where, Z denotes the relative compaction and diagenesis of the deep/ultra-deep marine carbonate reservoir.

The porosity of the deep/ultra-deep marine carbonate reservoir is calculated as follows:

$$Z_1 = \Pi_{i=1}^n x_i / [1 - \phi_0 (1 - \Pi_{i=1}^n x_i)] \quad (4)$$

$$\phi = \phi_0 Z_1 \quad (5)$$

where, $\phi$ denotes a current porosity of the deep/ultra-deep marine carbonate reservoir, %, $\phi_0$ denotes an initial porosity of the deep/ultra-deep marine carbonate reservoir before compaction and diagenesis, %, and $Z_1$ denotes a relative change value of the porosity, dimensionless.

In addition, in order to characterize the evolution process of the porosity of the deep/ultra-deep marine carbonate reservoir with the burial depth thereof, the present invention proposes corresponding computer processing, and module application and graphic output.

1) Computer Processing

Block 1: Input 5 influence coefficients with corresponding degrees of influence.

Block 2: Generate 1,000 sets of random numbers for a simulation interval of the geological age of the deep/ultra-deep marine carbonate reservoir.

Block 3: Generate 1,000 sets of random numbers for a simulation interval of the burial depth of the deep/ultra-deep marine carbonate reservoir.

Block 4: Generate 1,000 sets of random numbers for a simulation interval of the dynamic deformation experienced by the deep/ultra-deep marine carbonate reservoir after formation.

Block 5: Generate 1,000 sets of random numbers for a simulation interval of the formation temperature.

Block 6: Generate 1,000 sets of random numbers for a simulation interval of the homogeneity coefficient of the deep/ultra-deep marine carbonate reservoir.

Block 7: Calculate a value Z of the relative compaction and diagenesis of the deep/ultra-deep marine carbonate reservoir according to Eq. 3.

Block 8: Calculate a relative change value Z1 of the porosity of the deep/ultra-deep marine carbonate reservoir according to Eq. 4.

Block 9: Carry out a simulation of the porosity of the deep/ultra-deep marine carbonate reservoir according to Eq. 5.

Block 10: Output a fitted scatter plot of the relationship between the porosity and the burial depth of the deep/ultra-deep marine carbonate reservoir.

2) Module Application and Graphic Output:

Block 1: Fit the porosity and the burial depth of the deep/ultra-deep marine carbonate reservoir (polynomial) by a nonlinear fitting module method, and obtain a nonlinear equation and a 95% confidence interval parameter of the porosity and the burial depth of the deep/ultra-deep marine carbonate reservoir.

Block 2: Plot the evolution of the porosity parameter of the deep/ultra-deep marine carbonate reservoir with the burial depth thereof.

Located in Xinjiang in western China, the Tarim Basin is the largest petroliferous basin in China. It is a well-known development area of the Tianshan fold system and the Kunlun fold system. The area of the sedimentary basin is approximately $56 \times 10^4$ m². The Tarim Basin is rich in oil and gas, and it is the most important oil and gas supply area and the starting point of the famous First West-East Gas Pipeline Project of China. The proven oil and gas reserves of the Tarim Basin are $35.6 \times 10^8$ t oil equivalent, and the prospective resources thereof are $114 \times 10^8$ t, ranking third in the country's petroliferous basins. The strata below the Silurian in the Tarim Basin are marine carbonate deposits; moreover, the Ordovician below the target interval is the main storage and production layer of oil and gas and one of the target intervals most valued by explorers. In the Tazhong area, the Lower Ordovician carbonate rocks are found at burial depths of 3,356 m and 6,744 m.

Figure 3:
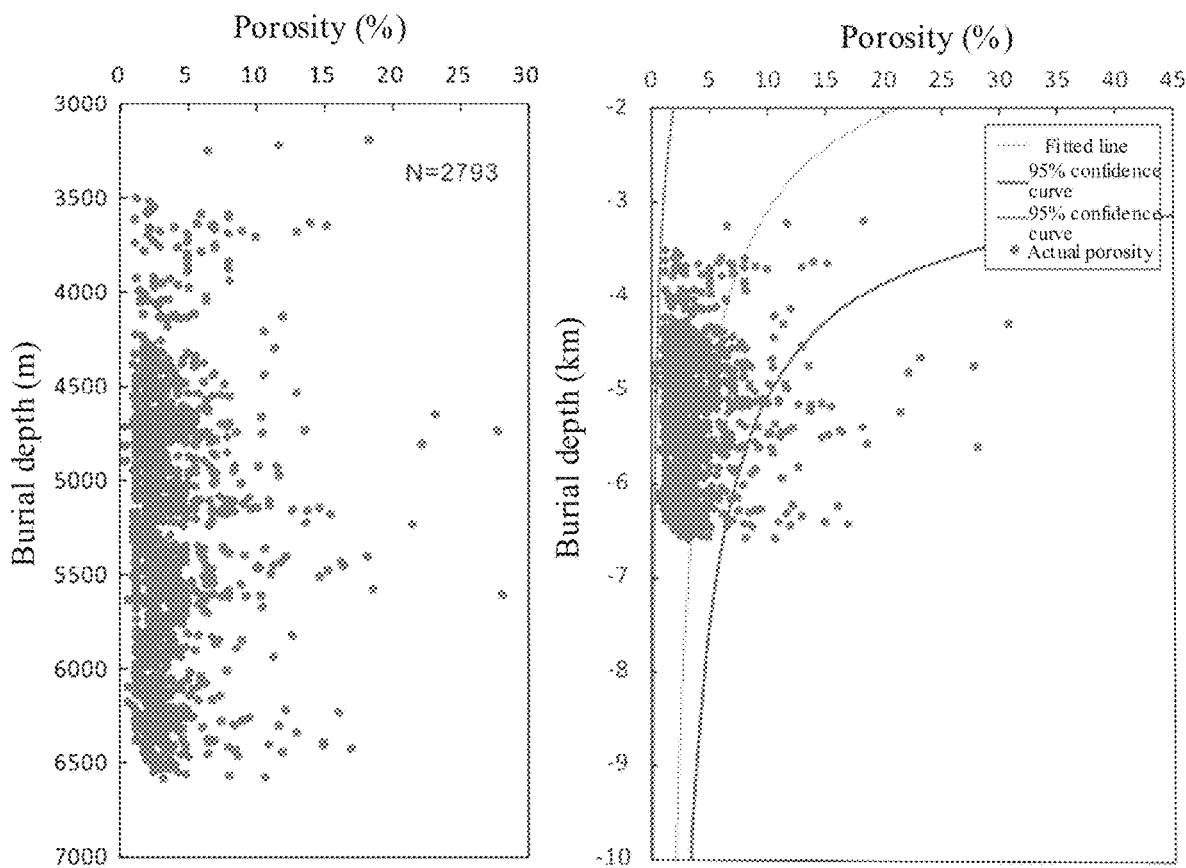
FIG. 3 shows a comparison between actual data and numerical simulation results of a change of a porosity of a Lower Ordovician carbonate rock with a burial depth thereof in the Tazhong area of the Tarim Basin in China according to an embodiment of the present invention.

In the present invention, the evolution process of the porosity of the Lower Ordovician marine carbonate reservoir in the Tazhong area of the Tarim Basin with the burial depth thereof is specifically characterized as follows:

Five physical and geological influence factors of the marine carbonate reservoir of the Lower Ordovician Yingshan Formation in the Tazhong area of the Tarim Basin are determined, including burial depth, geological age, formation temperature, dynamic deformation and homogeneity. The parameters required to characterize the evolution of the porosity of the marine carbonate reservoir with the burial depth thereof are determined, as shown in Table 3 below. According to steps S100 and S200, the change of the porosity of the Lower Ordovician marine carbonate reservoir in the Tazhong area from the surface to the burial depth of 10,000 m is simulated, as shown in FIG. 3. In the shallow layer of the basin, the porosity of the reservoir is relatively large, up to 20% at a burial depth below 2,000 m. In the middle layer of the basin, the porosity decreases greatly, only 8% to 12%. In the deep layer of the basin, the porosity decreases to 2% to 6%, but the decrease is small. The porosity decreases with the increasing burial depth, rapidly decreasing in the shallow layer and slowly decreasing in the deep layer. The porosity is very small at the burial depth of 10,000 m, only 1.2%.

TABLE 3

| Factor | Degree of influence | Influence coefficient | Value |
|---|---|---|---|
| Geological age A/Ma | | | 468-510 |
| Dynamic deformation | Strong | 0.968 | 2.6-2.73 |
| Burial depth H/km | | | 4.65-5.67 |
| Temperature ° C. | | | 140-162 |
| Homogeneity | Medium | 0.714 | 0.07-0.09 |

S300: Analyze, based on collected formation testing data and logging data, oil, gas and water layers encountered during drilling in a target interval, acquire ratios of oil, water and dry layers in each M % porosity interval, and acquire a relationship between a dry layer ratio and the porosity of the deep/ultra-deep marine carbonate reservoir, where the porosity interval is closed first and open last.

The drilling results show that, in general, a water layer is mainly encountered in a target interval with a small burial depth, an oil layer, a water layer and a dry layer are encountered in sequence in a deep layer, and a dry layer is 100% encountered in a deeper layer. According to the collected formation testing data and logging data, the oil, gas and water layers encountered in the target interval are analyzed. The ratios of the oil, water and dry layers in each M % porosity interval (closed first and open last) are acquired and the relationship between dry layer ratio and the porosity is acquired. In the present invention, M is a positive number greater than 0, and is preferably set to 0.5.

Figure 4:
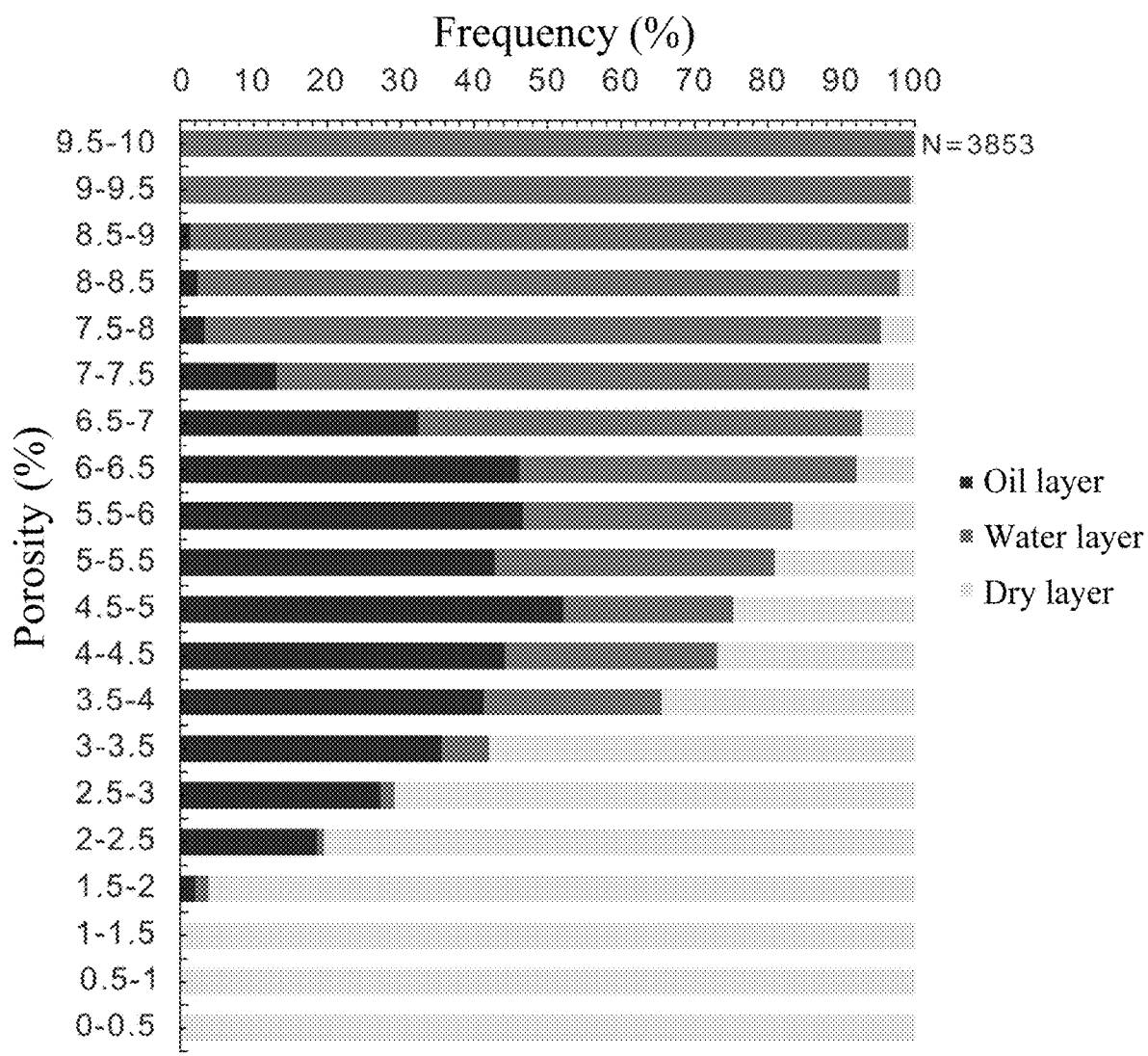
FIG. 4 shows changes of a fluid and a porosity in a Lower Ordovician marine carbonate reservoir in the Tazhong area of the Tarim Basin in China according to an embodiment of the present invention.

In this embodiment, according to the collected formation testing data and logging data, 3,853 oil, gas and water layers encountered in the target interval in the Tazhong area are analyzed and the ratios of the oil, water and dry layers in each 0.5% porosity interval are acquired. FIG. 4 visually shows the oil accumulation depth limit of the reservoir. When the porosity of the reservoir is greater than 8%, almost all the layers encountered are oil and water layers. When the porosity of the reservoir decreases, the ratios of the oil and water layers encountered decrease, and the dry layer ratio gradually increases. When the porosity of the reservoir decreases to an interval from 1.5% to 2% (closed first and open last), the dry layer ratio increases to 92%. When the porosity of the reservoir further decreases to an interval from 1% to 1.5%, the dry layer ratio reaches 100%.

S400: Recursively obtain, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determine an oil accumulation depth limit of the deep/ultra-deep marine carbonate reservoir.

In this embodiment, the relationship between the dry layer ratio and the burial depth is acquired by combining the relationship between the porosity and the burial depth determined in steps S100 and S200 and the relationship between the dry layer ratio and the porosity determined in step S300. The depth corresponding to a 100% dry layer ratio is the oil accumulation depth limit, based on which the oil accumulation depth limit of deep and ultra-deep marine carbonate reservoirs is determined.

Figure 5A:
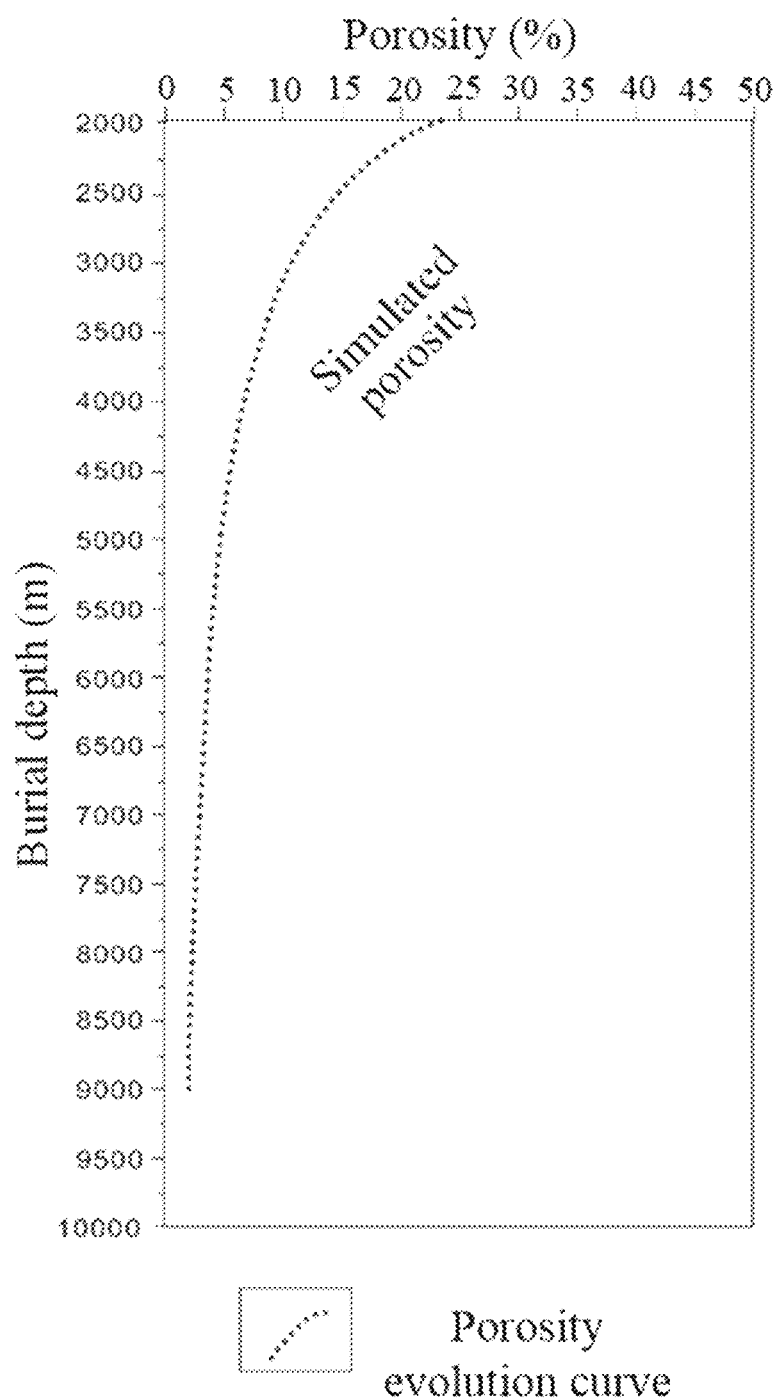
FIGS. 5A-5C show a prediction result of an oil accumulation depth limit of the Lower Ordovician carbonate reservoir in the Tazhong area of the Tarim Basin in China according to an embodiment of the present invention.
Figure 5B:
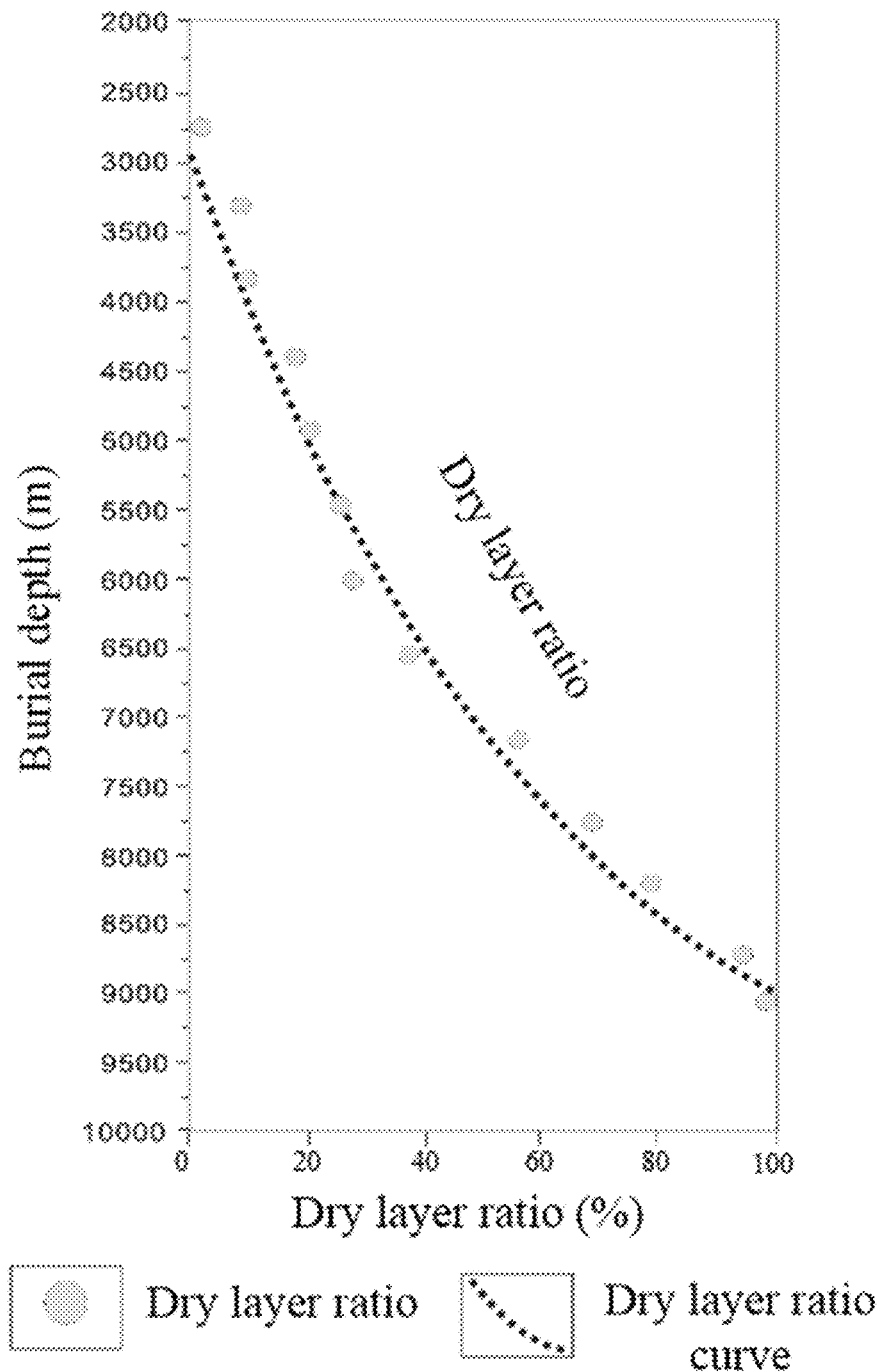
Figure 5C:
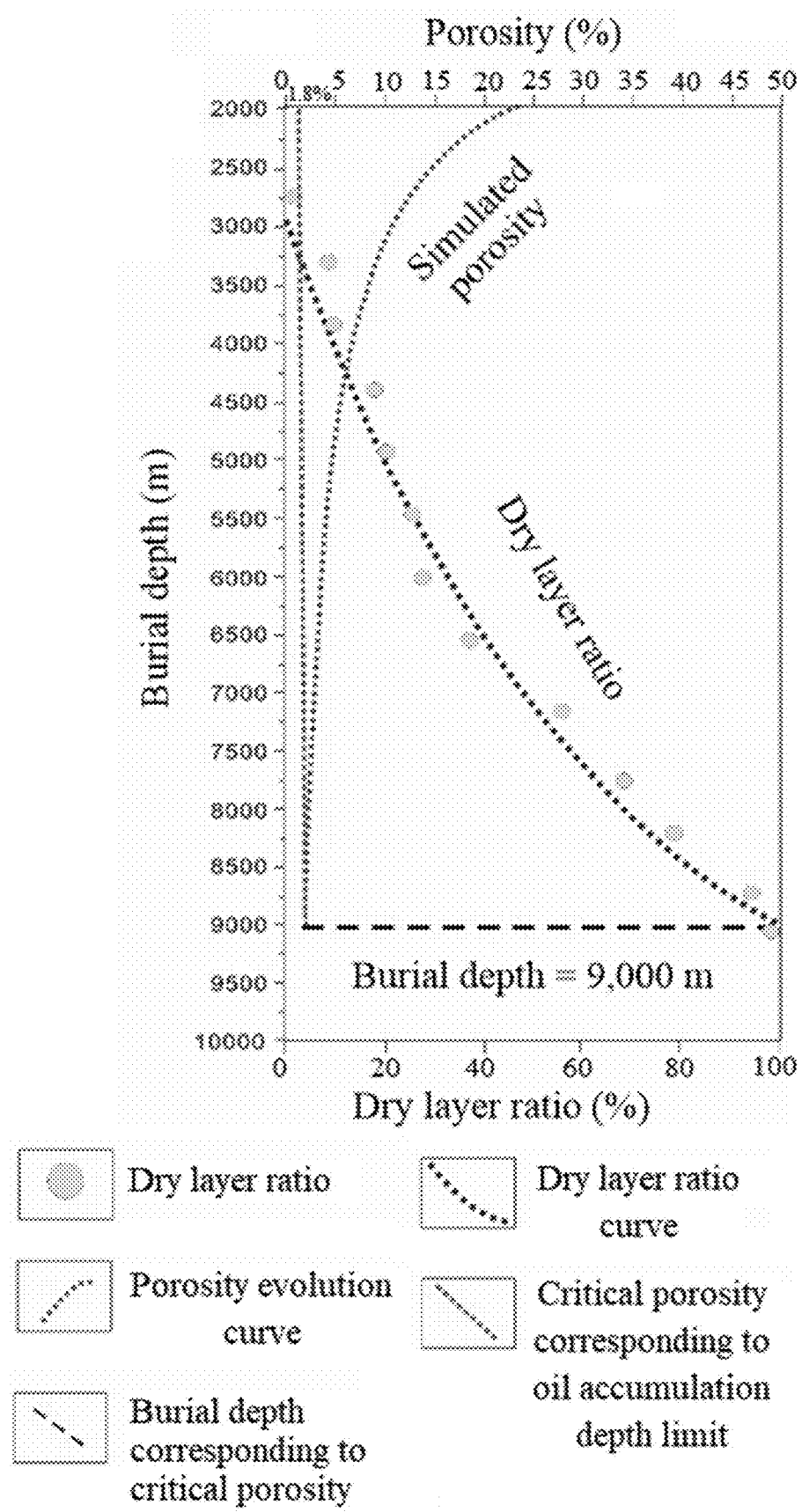

Firstly, the evolution process of the physical properties of the reservoir with the burial depth thereof is established (FIG. 5A). Secondly, according to the relationship between the dry layer ratio and the porosity and the relationship between the porosity and the burial depth, the relationship between the dry layer ratio and the burial depth is acquired (FIG. 5B). FIG. 5C shows the relationship between the dry layer ratio, the porosity and the burial depth. FIGS. 5A-5C show the prediction method and result of the oil accumulation depth limit of the Lower Ordovician carbonate reservoir in the Tazhong area. Based on this, the oil accumulation depth limit of the Lower Ordovician deep and ultra-deep carbonate reservoirs in the Tazhong area of the Tarim Basin is predicted to reach 9,000 m and the current maximum burial depth of the Lower Ordovician marine carbonate reservoirs in the Tazhong area does not exceed 8,000 m. This shows that it is feasible and promising to carry out deep carbonate reservoir exploration in this stratum.

Figure 2:
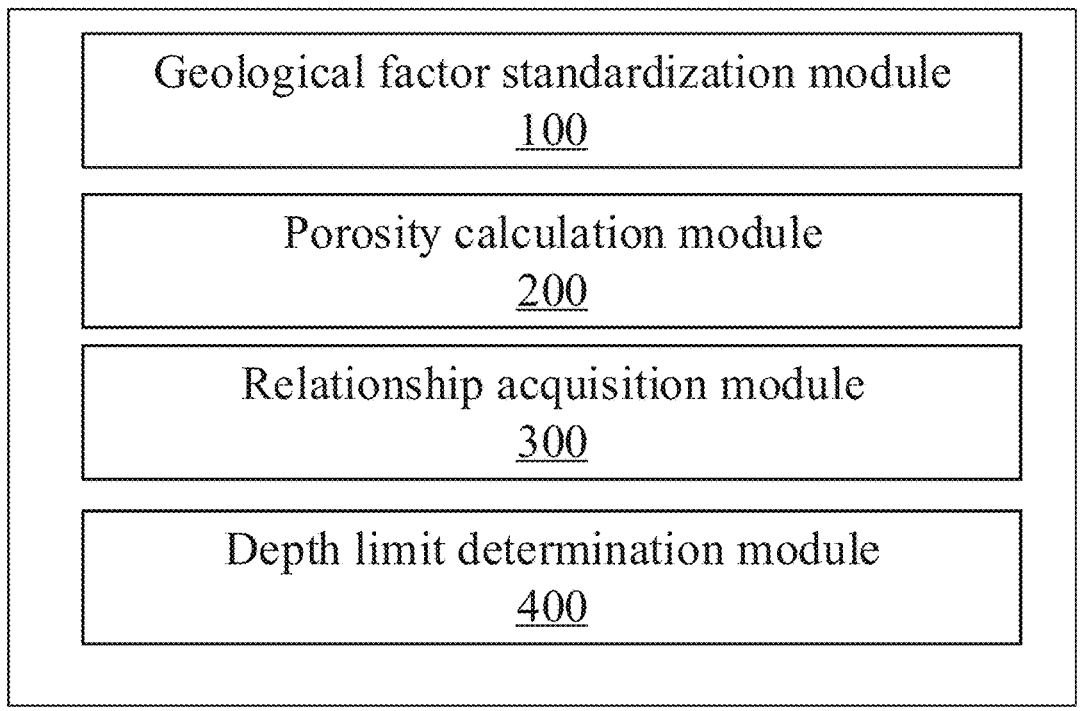
FIG. 2 is a block diagram of a system for predicting the oil accumulation depth limit of deep and ultra-deep marine carbonate reservoirs according to an embodiment of the present invention.

A second embodiment of the present invention proposes a system for predicting the oil accumulation depth limit of deep and ultra-deep marine carbonate reservoirs. As shown in FIG. 2, the system includes: a geological factor standardization module 100, a porosity calculation module 200, a relationship acquisition module 300, and a depth limit determination module 400.

The geological factor standardization module 100 is used for: obtaining geological factors acting on a porosity of a deep/ultra-deep marine carbonate reservoir and standardizing absolute values of the geological factors, where the geological factors include a geological age, a dynamic deformation, a burial depth, a formation temperature and homogeneity of the deep/ultra-deep marine carbonate reservoir.

The porosity calculation module 200 is used for: calculating modeling coefficients of a mathematical model of sediment compaction and diagenesis in a petroliferous basin, based on influence coefficients corresponding to the geological factors in combination with standardized absolute values of the geological factors, calculating, based on the modeling coefficients, relative compaction and diagenesis of the deep/ultra-deep marine carbonate reservoir by the mathematical model of the sediment compaction and diagenesis in the petroliferous basin, calculating the porosity of the deep/ultra-deep marine carbonate reservoir, and fitting a relationship between the porosity and the burial depth of the deep/ultra-deep marine carbonate reservoir.

The relationship acquisition module 300 is used for: analyzing, based on collected formation testing data and logging data, oil, gas and water layers encountered during drilling in a target interval, acquiring ratios of oil, water and dry layers in each M % porosity interval, and acquiring a relationship between a dry layer ratio and the porosity of the deep/ultra-deep marine carbonate reservoir, where the porosity interval is closed first and open last.

The depth limit determination module 400 is used for: recursively obtaining, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determining the oil accumulation depth limit of the deep/ultra-deep marine carbonate reservoir.

Those skilled in the art should clearly understand that, for convenience and brevity of description, reference is made to corresponding processes in the above method embodiments for specific working processes of the system, and details are not described herein again.

It should be noted that the system for predicting the oil accumulation depth limit of deep and ultra-deep marine carbonate reservoirs provided by the above embodiment is only described by taking the division of the above functional modules as an example. In practical applications, the above functions can be completed by different functional modules as required, that is, the modules or steps in the embodiments of the present invention are further decomposed or combined. For example, the modules of the above embodiments may be combined into one module, or may be further divided into multiple sub-modules to complete all or part of the functions described above. The names of the modules and steps involved in the embodiments of the present invention are only for distinguishing each module or step, and should not be regarded as improper limitations on the present invention.

A third embodiment of the present invention provides an electronic device, including: at least one processor and a memory communicatively connected to the at least one processor, where the memory stores an instruction executable by the processor and the instruction is executed by the processor to implement the above method for predicting the oil accumulation depth limit of deep and ultra-deep marine carbonate reservoirs.

Those skilled in the art can clearly understand that, for convenience and brevity of description, reference can be made to a corresponding process in the above method embodiment for specific working processes and related descriptions of the above electronic device. Details are not described herein again.

Those skilled in the art should be aware that the modules and method steps of the examples described in the embodiments disclosed herein may be implemented by electronic hardware, computer software or a combination thereof. The programs corresponding to software modules and method steps may be placed in random access memory (RAM), internal memory, read-only memory (ROM), electrically programmable ROM, electrically erasable programmable (ROM), registers, hard disk, removable disk, compact disc read-only memory (CD-ROM), or in any other form of storage medium known in the technical field. In order to clearly illustrate the interchangeability of THE electronic hardware and software, the composition and steps of each example are generally described in accordance with the function in the above description. Whether the functions are performed by electronic hardware or software depends on particular applications and design constraints of the technical solutions. Those skilled in the art may use different methods to implement the described functions for each specific application, but such implementation should not be considered to be beyond the scope of the present invention.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present invention are described with reference to the preferred implementations and drawings. Those skilled in the art should easily understand that the protection scope of the present invention is apparently not limited to these specific implementations. Those skilled in the art can make equivalent changes or substitutions to the relevant technical features without departing from the principles of the present invention, and the technical solutions after these changes or substitutions should fall within the protection scope of the present invention.

What is claimed is:

1. A method for predicting an oil accumulation depth limit of deep and ultra-deep marine carbonate reservoirs, comprising the following steps:
    1) obtaining geological factors acting on a porosity of a deep/ultra-deep marine carbonate reservoir and standardizing absolute values of the geological factors, wherein the geological factors comprise a geological age, a dynamic deformation, a burial depth, a formation temperature, and homogeneity of the deep/ultra-deep marine carbonate reservoir;
    2) calculating modeling coefficients of a mathematical model of sediment compaction and diagenesis in a petroliferous basin, based on influence coefficients corresponding to the geological factors in combination with standardized absolute values of the geological factors, calculating, based on the modeling coefficients, relative compaction and diagenesis of the deep/ultra-deep marine carbonate reservoir by the mathematical model of the sediment compaction and diagenesis in the petroliferous basin, calculating the porosity of the deep/ultra-deep marine carbonate reservoir, and fitting a relationship between the porosity and the burial depth of the deep/ultra-deep marine carbonate reservoir;
    3) analyzing, based on collected formation testing data and logging data, oil, gas and water layers encountered during drilling in a target interval, acquiring ratios of oil, water and dry layers in each M % porosity interval, and acquiring a relationship between a dry layer ratio and the porosity of the deep/ultra-deep marine carbonate reservoir, wherein M % porosity interval corresponds to an interval on a porosity evolution curve; and
    4) recursively obtaining, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determining the oil accumulation depth limit of the deep/ultra-deep marine carbonate reservoir.

2. The method according to claim 1, wherein the absolute values of the geological factors are standardized as follows:
    geological age of the deep/ultra-deep marine carbonate reservoir, A in units of Ma: $T_A=0.0125A$;
    dynamic deformation N in tectonostratigraphic units: $T_N=0.2+1.46 \log N$;
    burial depth of the deep/ultra-deep marine carbonate reservoir, H in units of km: $T_H=0.1H$;
    formation temperature of the deep/ultra-deep marine carbonate reservoir, t in units of $°$ C.: $T_t=0.005t$; and
    homogeneity of the deep/ultra-deep marine carbonate reservoir, S: $S=100\% * r_a/r_{max}$, wherein $r_a$ denotes an average pore throat radius, and $r_{max}$ denotes a maximum connected pore throat radius,
    wherein $T_A$, $T_N$, $T_H$, $T_t$, and S are standardized geological factors.

3. The method according to claim 2, wherein the modeling coefficients of the mathematical model of the sediment compaction and diagenesis in the petroliferous basin are calculated as follows:

$$x_i = \exp(-a_j T)$$

wherein, $x_i$ denotes the modeling coefficients, $a_j$ denotes the influence coefficients, and T denotes standardized geological factors.

4. The method according to claim 3, wherein the mathematical model of the sediment compaction and diagenesis in the petroliferous basin is:

$$U_t = U_0 \Pi_{i=1}^n x_i$$

wherein, $U_t$ denotes current sediment compaction and diagenesis, and $U_0$ denotes initial sediment compaction and diagenesis.

5. The method according to claim 4, wherein the relative compaction and diagenesis of the deep/ultra-deep marine carbonate reservoir is calculated as follows:

$$Z = U_t/U_0 = \Pi_{i=1}^n x_i$$

wherein, Z denotes the relative compaction and diagenesis of the deep/ultra-deep marine carbonate reservoir.

6. The method according to claim 5, wherein the porosity of the deep/ultra-deep marine carbonate reservoir is calculated as follows:

$$\phi = \phi_0 Z_1$$

$$Z_1 = \Pi_{i=1}^n x_i / [1 - \phi_0(1 - \Pi_{i=1}^n x_i)]$$

wherein, $\phi$ denotes a current porosity of the deep/ultra-deep marine carbonate reservoir, $\phi_0$ denotes an initial porosity of the deep/ultra-deep marine carbonate reservoir before compaction and diagenesis, and $Z_1$ denotes a relative change value of the porosity.

7. A system for predicting the oil accumulation depth limit of deep and ultra-deep marine carbonate reservoirs, comprising: a geological factor standardization module, a porosity calculation module, a relationship acquisition module, and a depth limit determination module, wherein
the geological factor standardization module is used for: obtaining geological factors acting on a porosity of a deep/ultra-deep marine carbonate reservoir and standardizing absolute values of the geological factors, wherein the geological factors comprise a geological age, a dynamic deformation, a burial depth, a formation temperature, and homogeneity of the deep/ultra-deep marine carbonate reservoir;
the porosity calculation module is used for: calculating modeling coefficients of a mathematical model of sediment compaction and diagenesis in a petroliferous basin, based on influence coefficients corresponding to the geological factors in combination with standardized absolute values of the geological factors, calculating, based on the modeling coefficients, relative compaction and diagenesis of the deep/ultra-deep marine carbonate reservoir by the mathematical model of the sediment compaction and diagenesis in the petroliferous basin, calculating the porosity of the deep/ultra-deep marine carbonate reservoir, and fitting a relationship between the porosity and the burial depth of the deep/ultra-deep marine carbonate reservoir;
the relationship acquisition module is used for: analyzing, based on collected formation testing data and logging data, oil, gas and water layers encountered during drilling in a target interval, acquiring ratios of oil, water and dry layers in each M % porosity interval, and acquiring a relationship between a dry layer ratio and the porosity of the deep/ultra-deep marine carbonate reservoir; and
the depth limit determination module is used for: recursively obtaining, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determining the oil accumulation depth limit of the deep/ultra-deep marine carbonate reservoir.

8. An electronic device, comprising:
at least one processor and a memory communicatively connected to the at least one processor, wherein
the memory stores instructions executable by the at least one processor and the instructions are executed by the at least one processor to implement a method for predicting the oil accumulation depth limit of deep and ultra-deep marine carbonate reservoirs, comprising steps of:
1) obtaining geological factors acting on a porosity of a deep/ultra-deep marine carbonate reservoir and standardizing absolute values of the geological factors, wherein the geological factors comprise a geological age, a dynamic deformation, a burial depth, a formation temperature, and homogeneity of the deep/ultra-deep marine carbonate reservoir;
2) calculating modeling coefficients of a mathematical model of sediment compaction and diagenesis in a petroliferous basin, based on influence coefficients corresponding to the geological factors in combination with standardized absolute values of the geological factors, calculating, based on the modeling coefficients, relative compaction and diagenesis of the deep/ultra-deep marine carbonate reservoir by the mathematical model of the sediment compaction and diagenesis in the petroliferous basin, calculating the porosity of the deep/ultra-deep marine carbonate reservoir, and fitting a relationship between the porosity and the burial depth of the deep/ultra-deep marine carbonate reservoir;
3) analyzing, based on collected formation testing data and logging data, oil, gas and water layers encountered during drilling in a target interval, acquiring ratios of oil, water and dry layers in each M % porosity interval, and acquiring a relationship between a dry layer ratio and the porosity of the deep/ultra-deep marine carbonate reservoir, wherein M % porosity interval corresponds to an interval on a porosity evolution curve; and
4) recursively obtaining, based on the relationship between the dry layer ratio and the porosity of the deep/ultra-deep marine carbonate reservoir and the relationship between the porosity and the burial depth of the deep/ultra-deep marine carbonate reservoir, a relationship between the dry layer ratio and the burial depth and determining the oil accumulation depth limit of the deep/ultra-deep marine carbonate reservoir.

9. The electronic device according to claim 8, wherein the absolute values of the geological factors are standardized as follows:
geological age of the deep/ultra-deep marine carbonate reservoir, A in units of Ma: $T_A = 0.0125A$;
dynamic deformation N in tectonostratigraphic units: $T_N = 0.2 + 1.46 \log N$;
burial depth of the deep/ultra-deep marine carbonate reservoir, H in units of km: $T_H = 0.1H$;
formation temperature of the deep/ultra-deep marine carbonate reservoir, t in units of °C.: $T_t = 0.005t$; and
homogeneity of the deep/ultra-deep marine carbonate reservoir, S: $S = 100\% * r_a/r_{max}$, wherein $r_a$ denotes an average pore throat radius, and $r_{max}$ denotes a maximum connected pore throat radius,
wherein $T_A$, $T_N$, $T_H$, $T_t$, and S are standardized geological factors.

10. The electronic device according to claim 9, wherein the modeling coefficients of the mathematical model of the sediment compaction and diagenesis in the petroliferous basin are calculated as follows:

$$x_i = \exp(-a_j T)$$

wherein, $x_i$ denotes the modeling coefficients, $a_j$ denotes the influence coefficients, and T denotes standardized geological factors.

11. The electronic device according to claim 10, wherein the mathematical model of the sediment compaction and diagenesis in the petroliferous basin is:

$$U_t = U_0 \Pi_{i=1}^n x_i$$

wherein, $U_t$ denotes current sediment compaction and diagenesis, and $U_0$ denotes initial sediment compaction and diagenesis.

12. The electronic device according to claim 11, wherein the relative compaction and diagenesis of the deep/ultra-deep marine carbonate reservoir is calculated as follows:

$$Z = U_t/U_0 = \Pi_{i=1}^n x_i$$

wherein, Z denotes the relative compaction and diagenesis of the deep/ultra-deep marine carbonate reservoir.

13. The electronic device according to claim 12, wherein the porosity of the deep/ultra-deep marine carbonate reservoir is calculated as follows:

$$\phi = \phi_0 Z_1$$

$$Z_1 = \Pi_{i=1}^n x_i / [1 - \phi_0(1 - \Pi_{i=1}^n x_i)]$$

wherein, $\phi$ denotes a current porosity of the deep/ultra-deep marine carbonate reservoir, $\phi_0$ denotes an initial porosity of the deep/ultra-deep marine carbonate reservoir before compaction and diagenesis, and $Z_1$ denotes a relative change value of the porosity.

* * * * *